United States Patent
Akamatsu et al.

(10) Patent No.: US 12,258,578 B2
(45) Date of Patent: Mar. 25, 2025

(54) AGENT FOR ACCELERATING MATURATION OR AGING OF CELLS

(71) Applicant: JUNTENDO EDUCATIONAL FOUNDATION, Bunkyo-Ku (JP)

(72) Inventors: Wado Akamatsu, Bunkyo-ku (JP); Takahiro Shiga, Bunkyo-ku (JP); Naoko Kuzumaki, Shinagawa-ku (JP); Hideyuki Okano, Shinjuku-ku (JP)

(73) Assignee: JUNTENDO EDUCATIONAL FOUNDATION, Bunkyo-ku (JP)

( * ) Notice: Subject to any disclaimer, the term of this patent is extended or adjusted under 35 U.S.C. 154(b) by 272 days.

(21) Appl. No.: 16/600,117

(22) Filed: Oct. 11, 2019

(65) Prior Publication Data

US 2020/0318064 A1    Oct. 8, 2020

(30) Foreign Application Priority Data

Apr. 8, 2019   (JP) ................................. 2019-073340

(51) Int. Cl.
| | |
|---|---|
| *C12N 5/00* | (2006.01) |
| *C12N 5/0735* | (2010.01) |
| *C12N 5/074* | (2010.01) |
| *C12N 5/077* | (2010.01) |
| *C12N 5/079* | (2010.01) |
| *G01N 33/50* | (2006.01) |

(52) U.S. Cl.
CPC ......... *C12N 5/0618* (2013.01); *C12N 5/0606* (2013.01); *C12N 5/0607* (2013.01); *C12N 5/0656* (2013.01); *G01N 33/5058* (2013.01); *G01N 33/5073* (2013.01); *C12N 2506/08* (2013.01); *C12N 2506/1307* (2013.01)

(58) Field of Classification Search
USPC ...................................................... 435/325
See application file for complete search history.

(56) References Cited

PUBLICATIONS

Golding (Cell cycle, 2012, vol. 11, No. 6, p. 1167-1173).*
Golding (Mol Cancer Ther, 2009, vol. 8, No. 10, p. 2894-2902).*
Kang (Nature Chem. Biol., 2017, vol. 13, p. 616-623).*
Justine D. Miller, et al. "Human iPSC-Based Modeling of Late-Onset Disease via Progerin-Induced Aging", Cell Stem Cell. 2013. 13(6): 691-705.
Elsa Vera, et al. "Generating Late-Onset Human iPSC-Based Disease Models by Inducing Neuronal Age-Related Phenotypes through Telomeras Manipulation", Cell Reports, 2016, 17(4): 1184-1182.
Takahiro Shiga et al., "The 41$^{st}$ Annual Meeting of the Molecular Biology Society of Japan", Abstract,[1LBA-085].
Takahiro Shiga et al., ISSCR 2019 T-1016.
Kinoshita et al, "Nuclear Contour Irregularity and Abnormal Transporter Protein Distribution in Anterior Horn Cells in Amyotrophic Lateral Sclerosis", *J Neuropathol Exp Neurol*, 2009, vol. 68, No. 11, pp. 1184-1192.
Liu et al, "Progressive degeneration of human neural stem cells caused by pathogenic LRRK2", *Nature*, 2012, vol. 491, 11 pages.
Sheffield et al, "Nuclear Pore Complex Proteins in Alzheimer Disease", *J. Neuropathol Exp Neurol*, 2006, vol. 65, No. 1, pp. 45-54.
Frost et al, "Lamin Dysfunction Mediates Neurodegeneration in Tauopathies", Curr Biol., 2016, vol. 26 (1), 16 pages.
Woerner et al, "Cytoplasmic protein aggregates interfere with nucleocytoplasmic transport of protein and RNA", *Science*, 2016, vol. 351, Abstract—2 pages.
He et al, "Amyloid-$\beta_{1-42}$ oligomer accelerates senescence in adult hippocampal neural stem/progenitor cells via formylpeptide receptor 2", *Cell Death and Disease*, 2013, vol. 4, e924.

* cited by examiner

*Primary Examiner* — Michael C Wilson
(74) *Attorney, Agent, or Firm* — Oblon, McClelland, Maier & Neustadt, L.L.P.

(57) ABSTRACT

Provided is an agent for accelerating maturation or aging of cells. An agent for accelerating maturation or aging of cells, comprising KU-60019 as an active ingredient.

3 Claims, 8 Drawing Sheets
(8 of 8 Drawing Sheet(s) Filed in Color)

AGENT FOR ACCELERATING MATURATION OR AGING OF CELLS

BACKGROUND OF THE INVENTION

Field of the Invention

The present invention relates to an agent for accelerating maturation or aging of cells and an efficient pathogenic phenotype detection for a neurodegenerative disease to develop screening methods for therapeutic agents.

Description of the Related Art

Late-onset neurodegenerative diseases such as amyotrophic lateral sclerosis (ALS), Parkinson's disease and Alzheimer's disease are diseases in which a specific subtype of neurons in the central nervous system degenerates and eventually dies. Although the cause of these neurodegenerative diseases is related to cellular aging, the most pathogenic mechanisms are still unclear. Therefore, a highly reproducible disease modeling is needed to develop therapeutic drugs for these neurodegenerative diseases.

Moreover, highly versatile culture cells for research include fibroblasts. Although fibroblasts are useful in order to study the aging mechanisms in vivo, a technique for rapidly inducing cell aging is important for such studies.

In neurodegenerative disease model studies using neural cells differentiated from patient-derived iPS cells, the maturation of induced neural cells requires a relatively long culture period, and even if the culture is performed for a long period such as 70 to 100 days, it is often difficult to observe disease-specific phenotypes (such as the aggregation of abnormal proteins) that take decades to develop in humans. In order to solve this problem, techniques for accelerating aging of iPS cell-derived nerve cells using methods such as external gene transfer (progeria gene; progerin) (Non Patent Literature 1) and inhibition of telomere synthetase (Non Patent Literature 2), have been reported.

CITATION LIST

Non Patent Literature

Non Patent Literature 1: Cell Stem Cell. 2013, 13(6): 691-705
Non Patent Literature 2: Cell Reports. 2016, 17(4): 1184-1192

SUMMARY OF THE INVENTION

However, since these methods require specific techniques for gene transfer and thus are not simple and their effects are not so strong, they can only weakly accelerate cell aging.

Therefore, an object of the present invention is to provide an agent for accelerating maturation or aging of various cells, a method for accelerated detection of pathogenic phenotypes in neurodegenerative disease models using the agent, and a screening method for a therapeutic drug for a neurodegenerative disease using the agent.

The present inventors searched for a low-molecular compound that accelerates cell maturation or aging using a culture system of nerve cells or fibroblasts, and as a result, they found that KU-60019 has an extremely potent cell maturation or aging accelerating action. Furthermore, they found that the Parkinson's disease phenotype in nerve cells is detected in 7 days of culture when nerve cells derived from iPS cells of a Parkinson's disease patient are cultured in a medium containing KU-60019, and that this culture system is therefore useful as a screening model for a therapeutic drug for a neurodegenerative disease, and completed the present invention.

That is, the present invention provides the following [1] to [10].

[1] An agent for accelerating maturation or aging of cells, comprising KU-60019 as an active ingredient.
[2] The agent for accelerating maturation or aging according to [1], wherein the cells are nerve cells or fibroblasts.
[3] The agent for accelerating maturation or aging according to [1], wherein the cells are cells derived from pluripotent stem cells.
[4] The agent for accelerating maturation or aging according to [2], wherein the cells are cells derived from pluripotent stem cells.
[5] A method for accelerating maturation or aging of cells, comprising culturing cells in a medium containing KU-60019.
[6] The method for accelerating maturation or aging according to [5], wherein the cells are nerve cells or fibroblasts.
[7] The method for accelerating maturation or aging according to [5], wherein the cells are cells derived from pluripotent stem cells.
[8] The method for accelerating maturation or aging according to [6], wherein the cells are cells derived from pluripotent stem cells.
[9] A screening method for a therapeutic drug for a neurodegenerative disease, comprising culturing nerve cells in a medium containing a test substance and KU-60019.
[10] The screening method according to [9], wherein the nerve cells are nerve cells derived from pluripotent stem cells.

When the agent for accelerating maturation or aging of cells of the present invention is used, nerve cells differentiated from pluripotent stem cells represented by iPS cells and fibroblasts mature and age in an extremely short period of time. In addition, if iPS cells derived from a patient with a neurodegenerative disease are cultured in a medium containing the agent for accelerating maturation or aging of cells of the present invention, the phenotype of the neurodegenerative disease is detected in an extremely short period of time. Thus, this culture system enables the selection of a therapeutic agent for a neurodegenerative disease through screening. When the agent for accelerating maturation or aging of cells of the present invention is allowed to act on fibroblasts for aging, aged cells can be obtained in a shorter time than conventionally, which allows to efficiently conduct aging research.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

The active ingredient of the agent for accelerating maturation or aging of cells of the present invention is KU-60019.

KU-60019 is a compound represented by the following formula (1).

(1)

KU-60019 is known to be an ATM inhibitor, and ATM is a causative gene of ataxia telangiectasia, which is a progeria. In recent reports, it has been reported that in ATM-deficient mice and ATM-deficient nematodes, nerve cell death is induced by the reduction of intracellular $NAD^+$, which shortens the life span (Cell Metabolism. 2016). However, since the maturation or aging accelerating effect of KU-60019 on nerve cells occurs in about 7 days of culture, the effect cannot be explained by the ATM inhibitory action alone.

In addition, the excellent maturation or aging accelerating effect as in the present invention is specific to KU-60019, since the effect cannot be obtained with KU55933, which is another ATM inhibitor, or NU7441, which is a DNA-PK inhibitor.

In the present invention, the cells as a target of maturation or aging acceleration may be any culturable cells, but nerve cells, fibroblasts, Hela cells (cells derived from human cervical cancer), SHSY5 cells (human neuroblastoma) are preferable.

The nerve cells in the present invention may be any type of nerve cell, but they are preferably nerve cells involved in a neurodegenerative disease. For example, when dopaminergic neurons are used, it is possible to select a therapeutic drug for Parkinson's disease or a neurodegenerative disease in which cognitive function is reduced.

Moreover, the fibroblasts in the present invention may be normal fibroblasts, and skin-derived fibroblasts are preferable in terms of easy availability.

In the present invention, the cells as a target of maturation or aging acceleration are preferably cells derived from pluripotent stem cells. Here, pluripotent stem cells include embryonic stem cells (ES cells), ntES cells and iPS cells, but iPS cells are more preferable. Among iPS cells, human iPS cells are preferable. As iPS cells to be used for the screening for a therapeutic agent for a neurodegenerative disease, iPS cells derived from a patient with a neurodegenerative disease are preferable.

In the present invention, neurodegenerative diseases are diseases in which a specific subtype of neurons in the central nervous system is gradually damaged and lost. Examples thereof include amyotrophic lateral sclerosis (ALS), Parkinson's disease, Alzheimer's disease, progressive supranuclear palsy (PSP), Huntington's disease, multiple system atrophy and spinocerebellar degeneration (SCD).

In the present invention, in order to accelerate the maturation or aging of cells, the cells are cultured in a medium containing KU-60019.

The concentration of KU-60019 in the medium is preferably 0.1 μM to 50 μM and more preferably 0.5 μM to 10 μM from the viewpoint of accelerating maturation or aging.

In addition, the medium to be used for culture differs depending on the differentiation process of the cells to be used, but KBM Neural Stem Cell (KOHJIN BIO) is used as a basal medium. In the generation of nerve cells from stem cells, it is preferable to use the basal medium added with a fibroblast growth factor (FGF2), a TGF-β type I receptor inhibitor (e.g., SB431542), a ROCK inhibitor (e.g., Y27632), a Sonic Hedgehog pathway agonist (e.g., Purmorphamine), a GSKβ inhibitor (e.g., CHIR99021) and the like for culture.

The concentration of fibroblast growth factor in the medium is preferably 10 to 40 ng/μL and more preferably 20 ng/μL. Moreover, the concentration of SB431542 in the medium is preferably 1 to 5 μM and more preferably 2 μM. The concentration of Y27632 in the medium is preferably 1 to 50 μM and more preferably 10 μM. The concentration of Purmorphamine in the medium is preferably 1 to 5 μM and more preferably 2 μM. The concentration of CHIR99021 in the medium is preferably 1 to 8 μM and more preferably 3 μM.

The culture conditions for generating nerve cells from stem cells are more preferably 5% $CO_2$, 4% $O_2$, and 35 to 40° C.

In addition, in the differentiation induction into nerve cells and maturation or aging of cells, it is preferable to use the basal medium added with a γ-secretase inhibitor (for example, DAPT), glial cell line-derived neurotrophic factor (GDNF), brain-derived neurotrophic factor (BDNF), transforming growth factor (TGFβ), dbcAMP, ascorbic acid (AA) and the like for culture.

Here, the concentration of DAPT in the medium is preferably 1 to 50 µM and more preferably 10 µM. The concentration of GDNF in the medium is preferably 10 to 50 ng/µL and more preferably 20 ng/µL. The concentration of BDNF in the medium is preferably 10 to 50 ng/µL and more preferably 20 ng/µL. The concentration of TGFβ in the medium is preferably 0.2 to 5 ng/µL and more preferably 1 ng/µL. The concentration of dbcAMP in the medium is preferably 0.1 to 3 mM and more preferably 0.5 mM. The concentration of AA in the medium is preferably 0.1 to 1 mM and more preferably 0.2 mM.

The culture conditions for accelerating maturation or aging of nerve cells are more preferably 5% $CO_2$, 4% $O_2$, and 35 to 40° C. The culture conditions for accelerating maturation or aging of fibroblasts are more preferably 5% $CO_2$, and 35 to 40° C.

If a medium added with KU-60019 is used, the differentiation of stem cells, for example nerve cell clusters (neurospheres), into nerve cells is sufficiently achieved in 7 to 17 days. Moreover, if a medium added with KU-60019 is used, the maturation or aging of nerve cells is sufficiently achieved in 7 to 17 days. The differentiation of stem cells into nerve cells can be confirmed by the reduction of Nestin and the quantification of tyrosine hydroxylase-positive cells, which is a specific marker of dopaminergic neurons (DAN). In addition, the maturation or aging of nerve cells can be confirmed by, for example, the degradation of Lamin B and excessive DNA damage.

The screening method for a therapeutic agent for a neurodegenerative disease of the present invention can be carried out by culturing nerve cells in a medium containing a test substance and KU-60019. The culture medium and the culture conditions are the same as in the method for accelerating maturation or aging of nerve cells. The test substance may be added to the medium in a predetermined amount.

The effect of suppressing maturation or aging of nerve cells by the test substance can be evaluated by comparing the degree of maturation or aging of nerve cells in the case of addition of the test substance, with that in the case of non-addition of the test substance.

EXAMPLES

Next, the present invention is further described in detail by showing examples.

Example 1

The screening for low-molecular compounds that accelerate differentiation and/or maturation of nerve cells was performed using a commercially available inhibitor library according to the following procedure, and compound KU-60019, which accelerates the maturation of nerve cells induced from human iPS cells, was identified.

Figure 1:
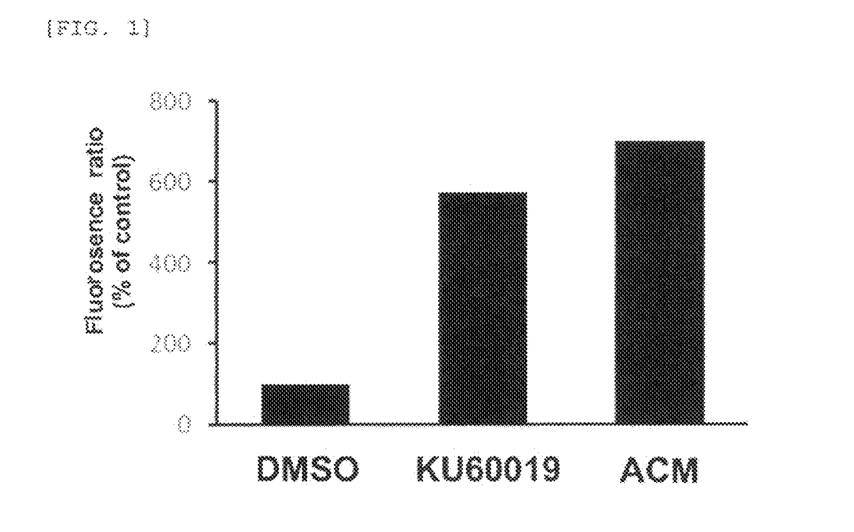
FIG. 1 shows the fluorescence intensity of a fluorescent reporter (GFP-Synapsin) of mature nerve cells; DMSO indicates dimethyl sulfoxide, KU60019 indicates KU-60019, and ACM indicates astrocyte conditioned medium.
Figure 2:
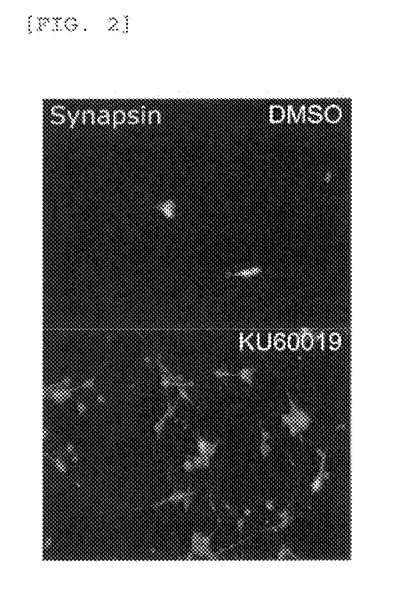
FIG. 2 shows the fluorescence intensity of a fluorescent reporter (GFP-Synapsin) of mature nerve cells; DMSO and KU-60019 are the same as in FIG. 1.

(1) A nerve cell cluster (Neurosphere) containing neural stem cells was prepared in suspension culture from iPS cells, passaged six times, and differentiated into nerves. A mature nerve cell-specific fluorescent reporter (GFP-Synapsin) was introduced using a lentiviral vector. Thereafter, the culture was switched to adherent culture, and 10 µM each of the low-molecular compound library (Sigma Aldrich) was added to the culture medium for neural differentiation, and the culture was performed for 17 days. The fluorescence intensity of GFP-Synapsin was quantified using an imaging cytometer (In cell analyzer). Using an astrocyte conditioned medium (ACM), which accelerates neural differentiation, as a control, compounds showing a fluorescence intensity closer to the control were selected (FIG. 1 and FIG. 2).

(2) The compound showing the highest fluorescence intensity among the compounds selected was KU-60019, which is an inhibitor of ATM that is a regulator of the DNA repair mechanism.

Example 2

The following experiment was performed to confirm the impact of KU-60019 on neural differentiation and/or maturation.

Figure 3:
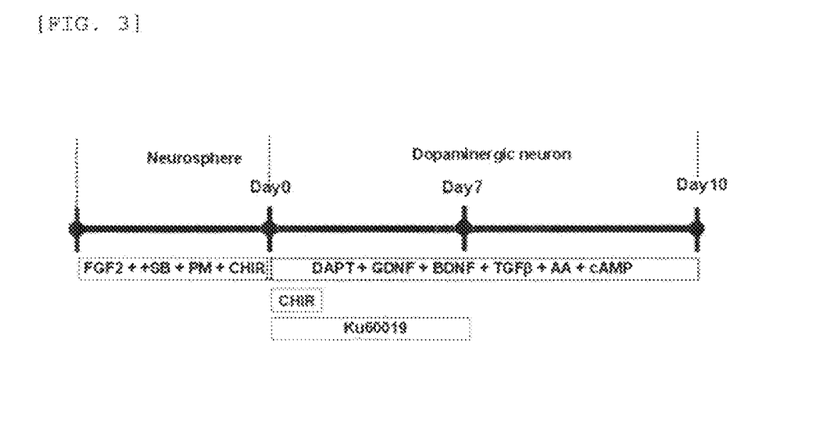
FIG. 3 shows the culture conditions and schedule of Example 2; FGF2: 20 ng/μL, SB431542 (SB): 2 μM, Purmorphamine (PM): 2 μM, CHIR99021 (CHIR): 3 μM; DAPT: 10 μM, GDNF: 20 ng/μL, TGFβ: 1 ng/μL, ascorbic acid (AA): 0.2 mM, and dbcAMP (cAMP): 0.5 mM.
Figure 4:
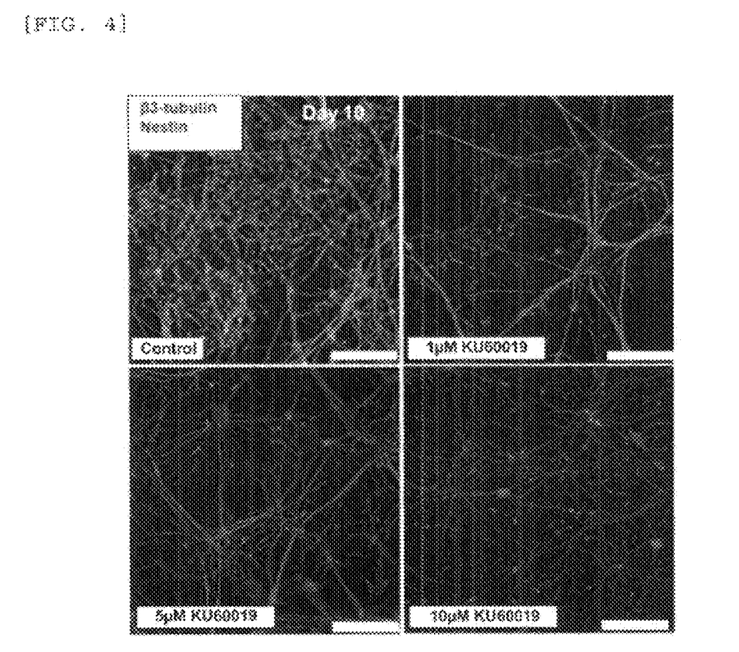
FIG. 4 shows the results of co-immunostaining using bIII tubulin (green) and Nestin (red) antibodies.
Figure 5:
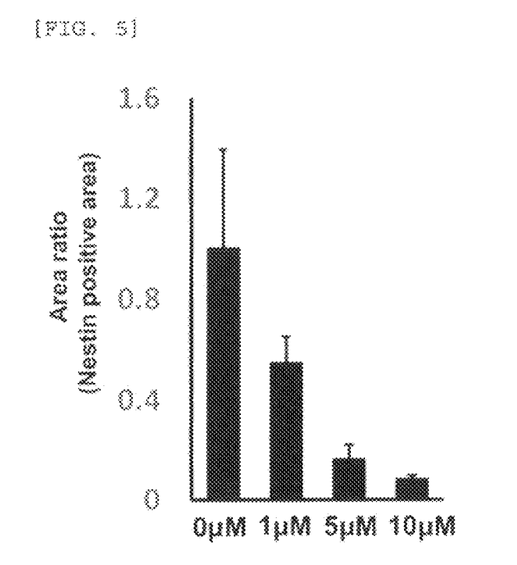
FIG. 5 shows the quantification results of the area of Nestin positive cells.

(1) When neural differentiation of human iPS cells into dopaminergic nerve cells was performed, KU-60019 was added to the neural differentiation medium at 1, 5 or 10 µM, followed by culture for 10 days, and the cells expressing Nestin, which is a marker of undifferentiated nervous system, were quantified to evaluate the differentiation efficiency (the culture conditions are shown in FIG. 3). As a result, the amount of Nestin-positive cells decreased depending on the concentration of KU-60019 (FIG. 4 and FIG. 5). This suggests that KU-60019 has an effect of accelerating differentiation of neural stem cells into nerve cells.

Figure 6:
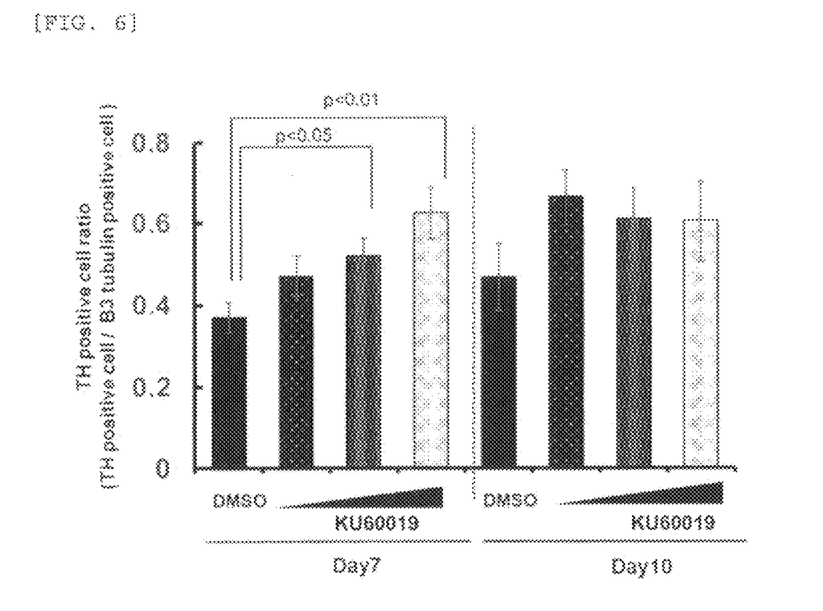
FIG. 6 shows the quantification results of tyrosine hydroxylase (TH) positive cells.

(2) In order to compare the amounts of dopaminergic neurons (DAN) differentiated by the same method as in (1), the quantification of tyrosine hydroxylase (TH) positive cells, which is a specific marker of mature DAN, was performed (FIG. 6). As a result, on day 7 of culture, DAN increased depending on the concentration of KU-60019, which suggests that KU-60019 increases the differentiation efficiency of DAN.

When the culture was further continued to day 10, this difference disappeared because all precursor cells were differentiated into DAN.

The following experiment was performed, considering that KU-60019 may accelerate aging in the differentiation from human iPS cells.

Figure 7:
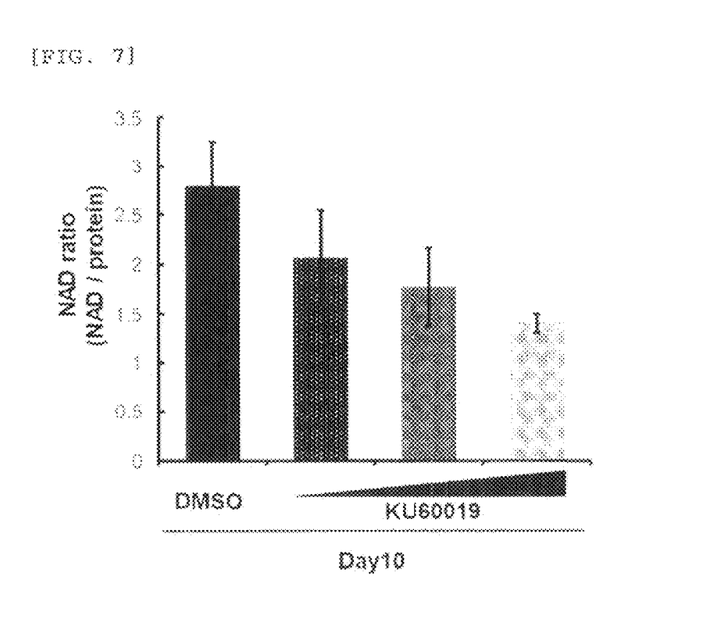
FIG. 7 shows the change in concentration of $NAD^+$ in iPS cell-derived nerve cells in the case of addition of KU-60019.

(3) The differentiation induction of DAN was performed using the same method as in (2), the cells were recovered after 10 days, and the intracellular $NAD^+$ concentration was measured using a colorimetric method (FIG. 7). As a result, the intracellular $NAD^+$ concentration decreased depending on the concentration of KU-60019. This suggests that KU-60019 accelerates cell aging.

Example 3

Excessive DNA damage and the breakdown of nuclear membrane structure associated thereto are known as a universal model of cell aging. In studies on aging models introduced with Progerin, it has been reported that the degradation of Lamin B (nuclear membrane protein) and excessive DNA damage (accumulation of γH2AX) occur in DAN in which cell aging has been accelerated (Cell Stem Cell. 2013). Based on this, it was verified whether the same thing is also caused in the aging model with KU-60019 addition.

Figure 8:
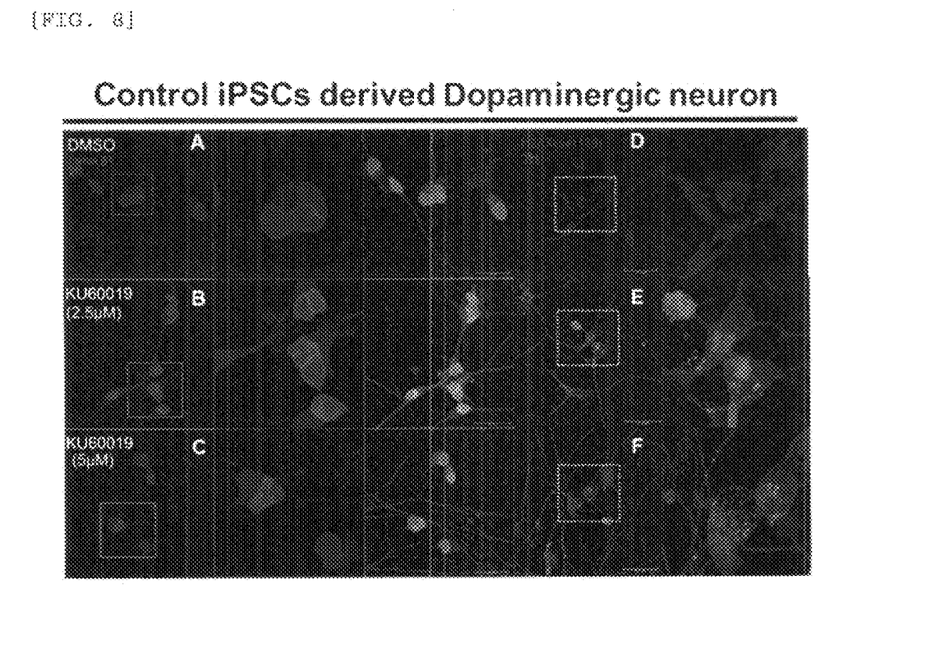
FIG. 8 shows the confirmation results of the aging phenotype of iPS cell-derived dopaminergic neurons (DAN) in the case of addition of KU-60019; (A-C) Influence on the nuclear membrane structure of DAN in the case of addition of KU-60019 and in the case of non-addition of KU-60019; Lamin B1 (green), TH (red); (D-F) Observation of DNA damage in DAN in the case of addition of KU-60019 and in the case of non-addition of KU-60019; γH2AX (green), TH (red).

(1) The differentiation induction of DAN from human iPS cells was performed using the same method as in Example 2(2), and immunostaining using a Lamin B1 antibody was performed on day 7 (FIGS. 8-A-C). As a result, it was found that the structure of Lamin B1 degraded in the case of addition of KU-60019. This suggests that the aging of neurons derived from human iPS cells is accelerated by the action of KU-60019.

(2) The differentiation induction of DAN from human iPS cells was performed using the same method as in Example 2(2), and immunostaining using a γH2AX (Ser139) antibody was performed on day 7 (FIGD. 8-D-F). As a result, it was found that γH2AX accumulated in the nucleus in the case of addition of KU-60019. This suggests that KU-60019 causes excessive DNA damage specific to the aging model.

Example 4

Since KU-60019 accelerates neural differentiation from human iPS cells and cell aging, it was verified whether the culture period required for phenotypic detection in DAN differentiated from Parkinson's disease-iPS cells could be shortened by the addition of KU-60019 to a conventional culture method. The culture periods required until phenotypic detection in the case of addition of KU-60019 and in the case of non-addition of KU-60019 were compared using iPS cells established from a patient with typical PARK 4 (α-synuclein duplication), which develops at a relatively old age (50s and beyond) among hereditary Parkinson's diseases.

Figure 9:
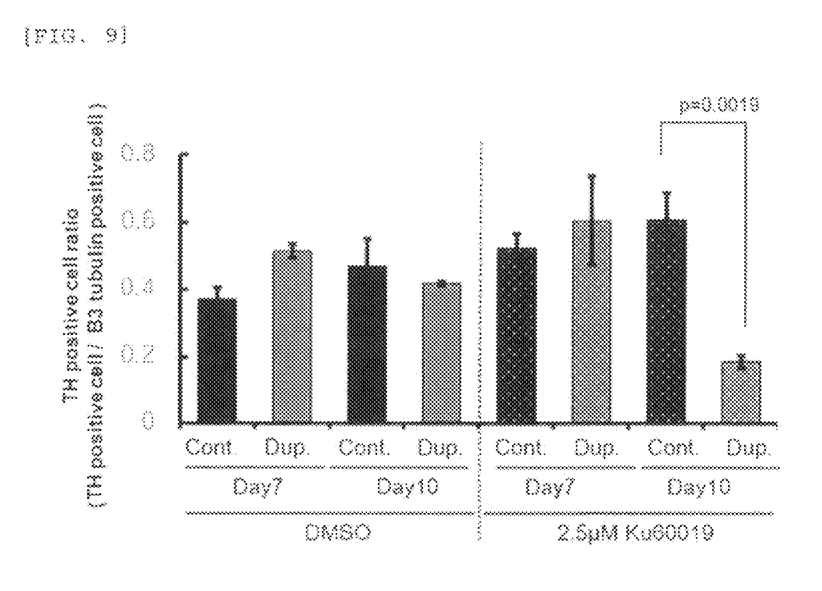
FIG. 9 shows the results of application to Parkinson's disease-iPSCs (measurement of the number of TH-positive cells in a PARK4-iPSCs-derived DAN culture).

(1) After performing the differentiation induction of PARK4-iPS cell-derived DAN using the same method as in Example 2(2), the cell loss of DAN was analyzed on days 7 and 10 using a TH antibody. As a result, on day 7 of culture, no significant increase in cell loss was observed in the case of addition of KU-60019 and in the case of non-addition of KU-60019, compared to normal control cells. The culture was further continued, and on day 10 of culture, no significant cell loss was observed in the non-KU-60019-added group as on day 7, but in the KU-60019-added group, it was confirmed that lost cells significantly increased compared to the normal control cells (FIG. 9).

These results indicate that when KU-60019 is added to the culture medium, the aging of iPS cell-derived nerve cells is accelerated, thus it is possible to detect, in a short period of time, delayed phenotypes which were difficult to detect with a conventional culture period.

Example 5

(Observation of Aging-Specific Nuclear Membrane Abnormalities in Human Fibroblasts By the Addition of KU60019)

Figure 10A:
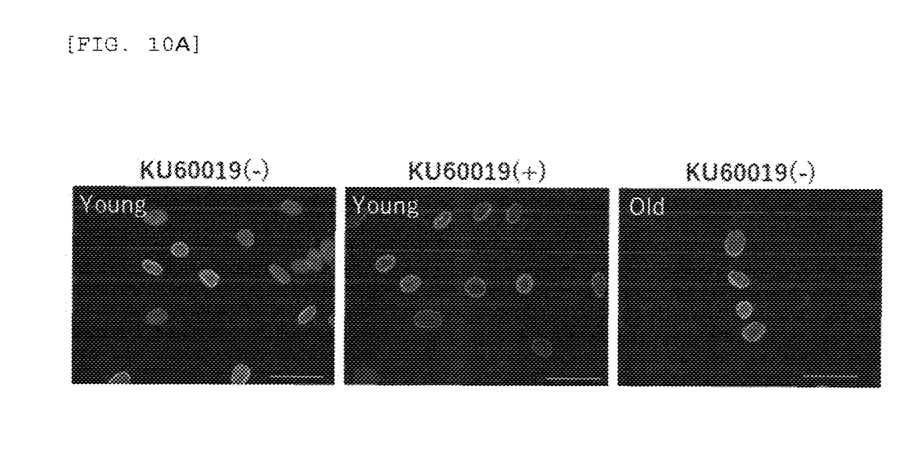
FIG. 10 shows the occurrence of aging-specific nuclear membrane abnormalities in human fibroblasts by the addition of KU60019.
Figure 10B:
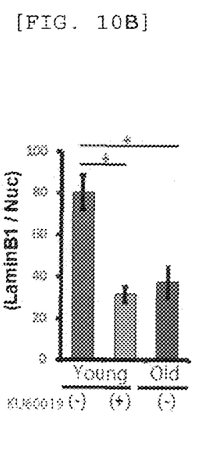

When KU60019 was allowed to act on fibroblasts derived from a young donor, aging-specific nuclear membrane abnormality (reduction of Lamin B1) was observed, showing an aging phenotype equivalent to that of fibroblasts derived from an old donor (Lamin B1 (green), Lamin A/C (red)) (FIG. 10A). The proportion of cells showing normal nuclear membrane structure in fibroblasts derived from a young donor was reduced by the action of KU60019 (mean±SEM, n=6, *$p<0.01$.) (FIG. 10B).

In fibroblasts collected from an old donor (51 years old), when compared with human fibroblasts collected from a young donor (18 years old), a decrease in Lamin B1, which is a nuclear membrane marker, as an aging-specific nuclear membrane abnormality is observed. When KU60019 was added to young donor-derived fibroblasts for 72 hours, a decrease in Lamin B1 was found, and nuclear membrane breakdown, which is an aging-specific phenotype, was observed (FIGS. 10A and 10B).

Example 6

(Increase in Aging-Specific Marker SA-Gal in Human Fibroblasts By the Addition of KU60019)

Figure 11A:
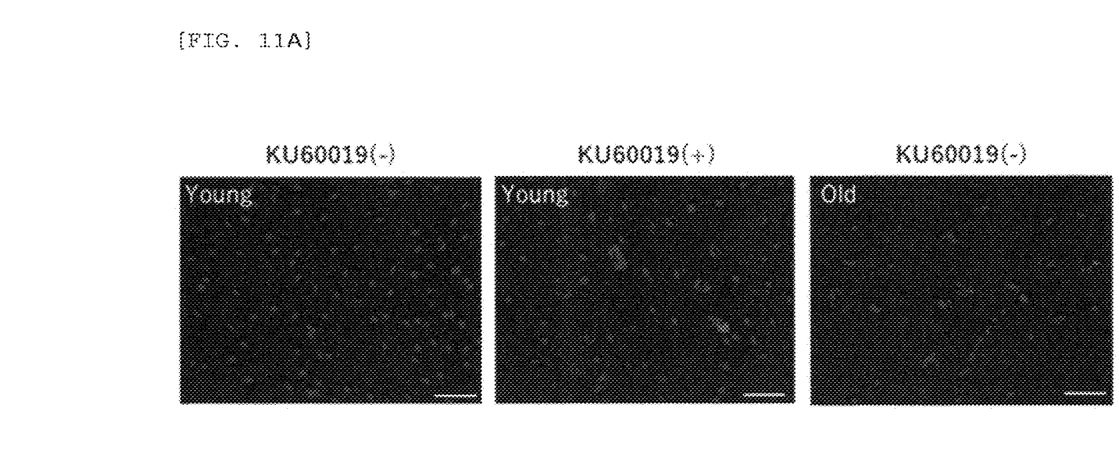
FIG. 11 shows the increase in aging-specific marker SA-Gal in human fibroblasts by the addition of KU60019.

When KU60019 was allowed to act on fibroblasts derived from a young donor, aging-specific marker SA-Gal (Senescence associated galactosidase) positive cells increased to a level equivalent to that in fibroblasts derived from an old donor and aging was accelerated (red: SA-Gal, blue: nuclear staining) (FIG. 11A). The SA-Gal intensity also increased similarly (mean±SEM, n=6, *$p<0.01$.) (FIG. 11B).

Figure 11B:
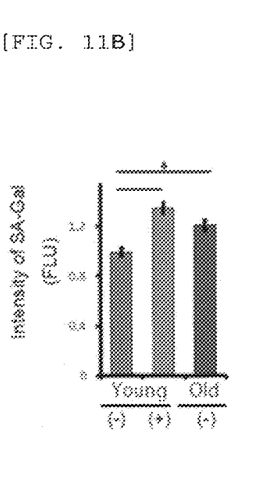

That is, in fibroblasts derived from an old donor, aging-specific marker SA-Gal (Senescence associated galactosidase) positive cells increased compared to fibroblasts derived from a young donor, but in fibroblasts derived from a young donor treated with KU60019, SA-Gal positive cells increased to a level equivalent to that in fibroblasts derived from an old donor (FIGS. 11A and 11B).

Example 7

(Acceleration of Cell Aging of SHSY5 Cells By the Addition of KU60019)

Figure 12A:
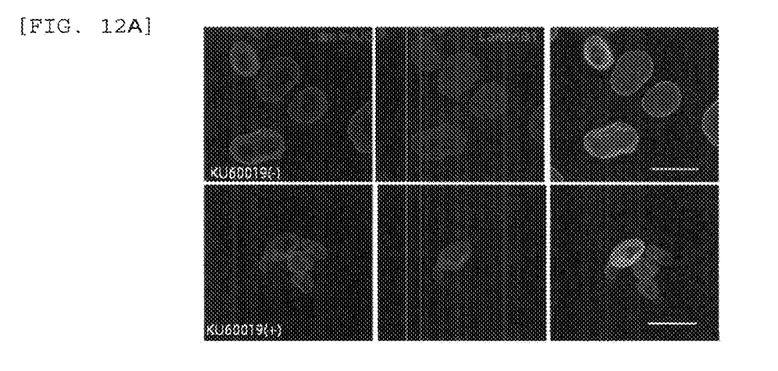
FIG. 12 shows the acceleration of cell aging of SHSY5 cells by the addition of KU60019.
Figure 12B:
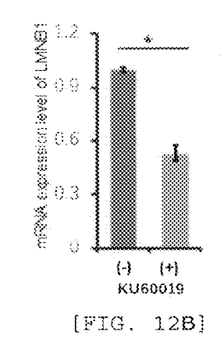
Figure 12C:
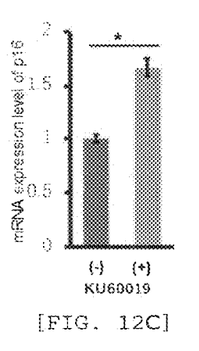
Figure 12D:
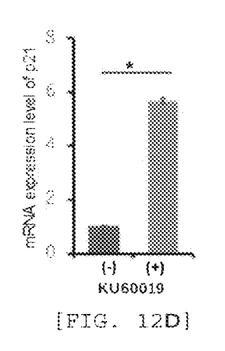

When KU60019 was allowed to act on SHSY5 cells, which are a cultured cell line derived from human neuroblastoma, aging-specific nuclear membrane abnormalities were caused (Green: Lamin B1, red: Lamin A/C, blue: nuclear staining) (FIG. 12A). A decrease in Lamin B1 (LMNB1) mRNA (FIG. 12B), an increase in aging marker p16 mRNA (FIG. 12C) and a decrease in aging marker p21 mRNA were detected by qPCR (mean±SEM, n=4, *$p<0.01$.) (FIG. 12D).

That is, also in SHSY5 (immortalized cell line of human nervous system), a breakdown of the nuclear membrane was observed by the addition of KU60019. In addition, since the expression of mRNA of Lamin B1 (LMNB1), which constitutes the nuclear membrane, was also reduced, it was confirmed that cell aging was accelerated. Regarding the expressions of mRNA of p16 and p21, which are aging-related genes used in the aging study of immortalized cells, it was confirmed that those were significantly elevated (FIGS. 12A-12D).

These results showed that the aging accelerating action of KU60019 is effective not only on iPS cell-derived neurons but also on cultured cells in general including them.

Example 8

It was verified whether a compound having a function similar to KU60019 had the same effect.

Figure 13:
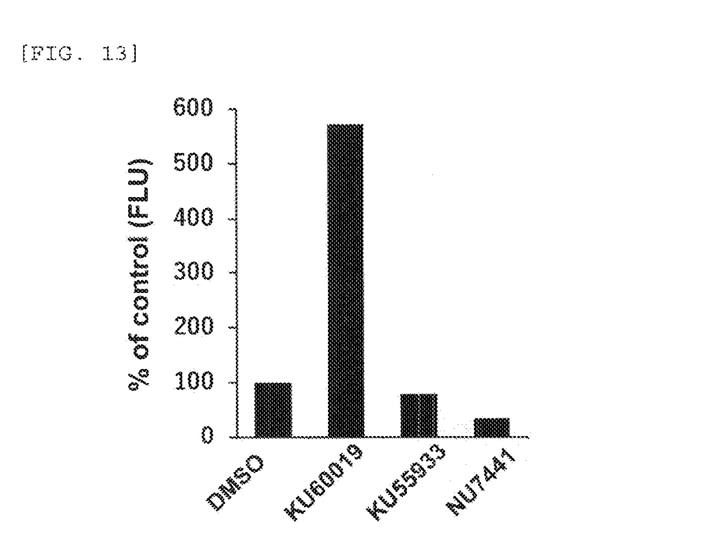
FIG. 13 shows the nerve cell maturation accelerating effects by KU60019, KU55933 and NU7441 (same method as in Example 1).

When KU60019 (ATM inhibitor), KU55933 (ATM inhibitor) or NU7441 (DNA-PK (factor related to DNA repair having a function similar to ATM) inhibitor) was allowed to act on human IPS cell-derived neurons in the same manner as in Example 1, acceleration of cell maturation was observed only in the cells to which KU60019 was added (FIG. 13). These results infer that, among ATM inhibitors and similar drugs, only KU60019 has a cell maturation accelerating or aging inducing action.

What is claimed is:

1. A method for accelerating maturation or aging of nontumor neural stem cells or nontumor fibroblasts, the method comprising:
   (A) i) differentiating isolated human pluripotent cells into nontumor neural stem cells; and
   ii) culturing the nontumor stem cells in a medium comprising 10 UM of KU60019 such that maturation or aging of the nontumor neural stem cells is accelerated as compared to nontumor neural stem cells cultured in the absence of KU60019; or (B) culturing nontumor fibroblasts from a human who is 18 years of age in a medium comprising 10 UM of KU60019 such that maturation or aging of the nontumor fibroblasts is accelerated as compared to nontumor fibroblasts cultured in the absence of KU60019.

2. The method of claim 1, wherein Lamin B degradation and DNA damage occurs in the nontumor neural stem cells obtained in A)ii).

3. The method of claim 1, wherein Lamin B degradation and DNA damage occurs in the nontumor fibroblasts obtained in B).

\* \* \* \* \*